(12) United States Patent
Imada

(10) Patent No.: US 10,179,828 B2
(45) Date of Patent: *Jan. 15, 2019

(54) CURABLE COMPOSITION FOR PERMANENT RESIST FILMS, AND PERMANENT RESIST FILM

(71) Applicant: DIC Corporation, Tokyo (JP)

(72) Inventor: Tomoyuki Imada, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/535,839

(22) PCT Filed: Nov. 19, 2015

(86) PCT No.: PCT/JP2015/082512
§ 371 (c)(1),
(2) Date: Jun. 14, 2017

(87) PCT Pub. No.: WO2016/114000
PCT Pub. Date: Jul. 21, 2016

(65) Prior Publication Data
US 2017/0349690 A1    Dec. 7, 2017

(30) Foreign Application Priority Data

Jan. 16, 2015 (JP) ................. 2015-006724

(51) Int. Cl.
| | | |
|---|---|---|
| *G06F 7/20* | (2006.01) | |
| *G03F 7/32* | (2006.01) | |
| *G03F 7/038* | (2006.01) | |
| *G03F 7/029* | (2006.01) | |
| *C08G 8/04* | (2006.01) | |
| *C07C 39/14* | (2006.01) | |
| *C07C 39/17* | (2006.01) | |
| *G03F 7/012* | (2006.01) | |
| *G03F 7/039* | (2006.01) | |
| *G03F 7/022* | (2006.01) | |
| *G03F 7/16* | (2006.01) | |
| *G03F 7/20* | (2006.01) | |

(52) U.S. Cl.
CPC .............. *C08G 8/04* (2013.01); *C07C 39/14* (2013.01); *C07C 39/17* (2013.01); *G03F 7/0125* (2013.01); *G03F 7/0226* (2013.01); *G03F 7/038* (2013.01); *G03F 7/039* (2013.01); *C07C 2603/92* (2017.05); *G03F 7/162* (2013.01); *G03F 7/168* (2013.01); *G03F 7/2004* (2013.01); *G03F 7/322* (2013.01)

(58) Field of Classification Search
None
See application file for complete search history.

(56) References Cited

U.S. PATENT DOCUMENTS

| | | | | |
|---|---|---|---|---|
| 5,302,672 | A * | 4/1994 | Ogura ................ | C07C 37/20 525/481 |
| 5,459,223 | A * | 10/1995 | Sue ..................... | C08G 8/04 257/E23.119 |
| 9,110,373 | B2 * | 8/2015 | Uchiyama ........... | C09D 161/06 |
| 9,828,457 | B2 * | 11/2017 | Imada ................. | G03F 7/0226 |
| 2002/0132095 | A1 * | 9/2002 | Fujii ................... | B32L 315/08 428/209 |
| 2014/0186776 | A1 * | 7/2014 | Uchiyama ........... | C09D 161/06 430/323 |
| 2014/0287241 | A1 * | 9/2014 | Satou .................. | C08G 59/02 428/418 |
| 2015/0185613 | A1 * | 7/2015 | Toyokawa ............ | G03F 7/26 438/704 |
| 2016/0159962 | A1 | 6/2016 | Imada et al. | |

(Continued)

FOREIGN PATENT DOCUMENTS

| | | | |
|---|---|---|---|
| JP | 61-069826 | * | 4/1986 |
| JP | 02-189326 | * | 7/1990 |

(Continued)

OTHER PUBLICATIONS

Li "Synthesis and properties of calix[4]naphthalenes", Thesis, Memorial University of Newfoundland, Canada (Jan. 1996).*

(Continued)

*Primary Examiner* — Martin J Angebranndt
(74) *Attorney, Agent, or Firm* — Locke Lord LLP

(57) ABSTRACT

A curable composition and a permanent resist film made using this curable composition are provided. The composition dissolves well in solvents, gives coatings superior in alkali developability, thermal decomposition resistance, light sensitivity, and resolution, and is particularly suitable for the formation of permanent resist films. Specifically, the composition is a curable composition for permanent resist films and contains a phenolic hydroxyl-containing compound (A) that has a molecular structure represented by structural formula (1):

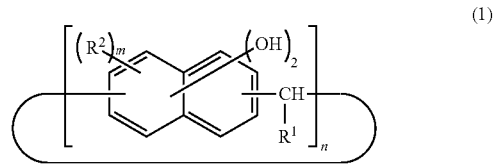

(1)

(where $R^1$ is hydrogen, alkyl, or aryl, and n is an integer of 2 to 10; $R^2$ is alkyl, alkoxy, aryl, aralkyl, or halogen, and m is an integer of 0 to 4; if m is 2 or more, the plurality of $R^2$s may be the same or different from one another, and may be bonded to either of the two aromatic rings in the naphthylene structure) and a photosensitizer (B1) or curing agent (B2).

19 Claims, 4 Drawing Sheets

(56) References Cited

U.S. PATENT DOCUMENTS

2017/0066703 A1* 3/2017 Imada .................. C07C 39/14
2017/0329226 A1* 11/2017 Imada .................. G03F 7/0392
2017/0334817 A1* 11/2017 Imada .................. C07C 39/14

FOREIGN PATENT DOCUMENTS

| JP | 05-132543 | * | 5/1993 |
| JP | 2009-244663 A | | 10/2009 |
| JP | 2010-277061 | * | 12/2010 |
| JP | 2012-162474 | * | 8/2012 |
| JP | 2012-162474 A | | 8/2012 |
| JP | 2013-067697 | * | 4/2013 |
| WO | 2009/119201 | * | 10/2009 |
| WO | 2014/038680 | * | 3/2014 |
| WO | 2015/008560 A1 | | 1/2015 |

OTHER PUBLICATIONS

International Search Report dated Feb. 9, 2016, issued for PCT/JP2015/082512.

* cited by examiner

CURABLE COMPOSITION FOR PERMANENT RESIST FILMS, AND PERMANENT RESIST FILM

TECHNICAL FIELD

The present invention relates to a curable composition that dissolves well in solvents, gives coatings superior in alkali developability, thermal decomposition resistance, light sensitivity, and resolution, and is particularly suitable for the formation of permanent resist films. The present invention also relates to a permanent resist film obtained using this curable composition.

BACKGROUND ART

Phenolic hydroxyl-containing compounds, used in adhesives, molding materials, paints, photoresist materials, raw materials for epoxy resins, curing agents for epoxy resins, etc., have also been utilized as the main ingredient of curable resin compositions in various fields of electrical and electronics engineering because of the superior characteristics they exhibit in the cured form, such as superb heat and moisture resistance.

In electrical and electronics engineering, curable compositions are used in, for example, permanent film applications. An example of a permanent film is a coating of a photosensitive resin formed on a component or interposed between components in a semiconductor device such as an IC or an LSI device or a display such as a thin display, and left in the product even after the product is completed. Specific examples of permanent films related to semiconductor devices include solder resists, packaging material, underfill, package bonding layers for circuit devices or other components, and layers for bonding integrated circuit devices to a circuit board. Specific examples of permanent films related to thin displays, typified by LCDs and OELDs, include protective coatings for thin-film transistors, protective coatings for liquid-crystal color filters, black matrix, and spacers.

When a curable composition is used to form permanent films, the composition needs to dissolve well in solvents, and the resulting coatings need to be superior in alkali developability, thermal decomposition resistance, light sensitivity, and resolution. An example of a composition for the production of permanent films is one that contains a novolac phenolic resin obtained through the polymerization of a phenolic hydroxyl-containing compound, such as phenol or naphthol, with an aldehyde (see, for example, PTL 1). However, coatings obtained using the composition disclosed in PTL 1 lack sufficient alkali developability, sensitivity, and resolution.

Another known example of a composition for the production of permanent films is one that contains a phenolic hydroxyl-containing compound that has the cylindrical structure called calixarene. The phenolic hydroxyl-containing compound can specifically be, for example, a naphthol-based calixarene obtained by reacting α-naphthol with formaldehyde in the presence of an alkaline earth metal hydroxide as a catalyst (see, for example, PTL 2). However, the naphthol-based calixarene disclosed in PTL 2 is not sufficiently soluble in organic solvents, and it is difficult to prepare therewith a composition for the production of permanent films.

CITATION LIST

Patent Literature

PTL 1: Japanese Unexamined Patent Application Publication No. 2009-244663
PTL 2: Japanese Unexamined Patent Application Publication No. 2012-162474

SUMMARY OF INVENTION

Technical Problem

An object of the present invention is therefore to provide a curable composition that dissolves well in solvents, gives coatings superior in alkali developability, thermal decomposition resistance, light sensitivity, and resolution, and is particularly suitable for the formation of permanent resist films, and to provide a permanent resist film obtained using this composition.

Solution to Problem

After extensive research to solve the above problem, the inventors have found, for example, that dihydroxynaphthalene-based calixarenes are significantly resistant to heat and highly soluble in commonly used solvents; that coatings obtained using these calixarenes are superior in heat resistance, light sensitivity, and resolution; and that compositions containing such a compound and a photosensitizer or curing agent are suitable for the formation of permanent resist films. The present invention was completed on the basis of these findings.

That is, the present invention provides a curable composition for permanent resist films. The composition contains a phenolic hydroxyl-containing compound (A) that has a molecular structure represented by structural formula (1):

[Chem. 1]

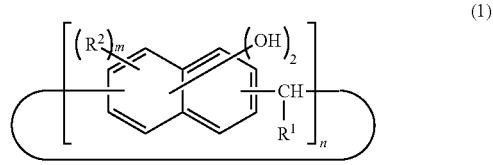

(1)

(where $R^2$ is hydrogen, alkyl, or aryl, and n is an integer of 2 to 10; $R^2$ is alkyl, alkoxy, aryl, aralkyl, or halogen, and m is an integer of 0 to 4; if m is 2 or more, the plurality of $R^2$s may be the same or different from one another, and may be bonded to either of the two aromatic rings in the naphthylene structure) and a photosensitizer (B1) or curing agent (B2).

The present invention also provides a permanent resist film. This permanent resist film is a cured form of the curable composition for permanent resist films.

Advantageous Effects of Invention

According to the present invention, a curable composition is provided that dissolves well in solvents, gives coatings superior in alkali developability, thermal decomposition resistance, light sensitivity, and resolution, and is particularly suitable for the formation of permanent resist films. A permanent resist film obtained using this curable composition is also provided.

DESCRIPTION OF EMBODIMENTS

Figure 1:
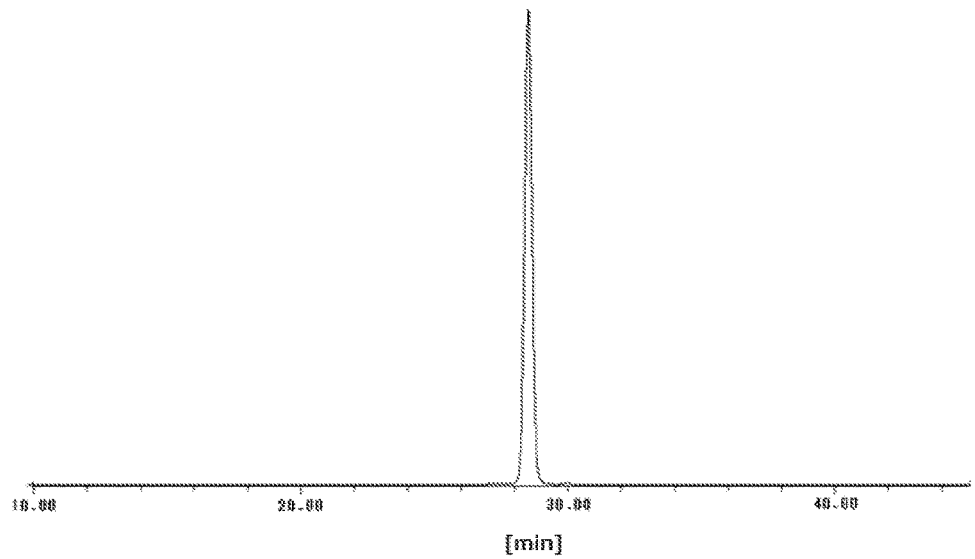
FIG. 1 is a GPC chart of phenolic hydroxyl-containing compound (A1), obtained in Synthesis Example 1.

A curable composition according to the present invention for permanent resist films contains a phenolic hydroxyl-containing compound (A) and a photosensitizer (B1) or curing agent (B2). The phenolic hydroxyl-containing compound (A) has a molecular structure represented by structural formula (1):

[Chem. 2]

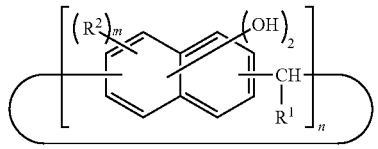

(1)

(where $R^2$ is hydrogen, alkyl, or aryl, and n is an integer of 2 to 10; $R^2$ is alkyl, alkoxy, aryl, aralkyl, or halogen, and m is an integer of 0 to 4; if m is 2 or more, the plurality of $R^2$s may be the same or different from one another, and may be bonded to either of the two aromatic rings in the naphthylene structure).

As mentioned above, the known calixarenes are not sufficiently compatible with materials such as commonly used organic solvents, other resin components, and additives. By contrast, phenolic hydroxyl-containing compounds represented by structural formula (1), having two hydroxyl groups in the naphthylene structure in structural formula (1) and therefore a high concentration of functional groups, are highly compatible with materials such as commonly used organic solvents, other resin components, and additives besides maintaining a high heat resistance characteristic of the calixarene structure.

Such a phenolic hydroxyl-containing compound (A) gives superior light sensitivity and resolution to photosensitive materials made therewith. With such a compound, therefore, it is possible to form permanent resist films highly sensitive to light and superior both in pre-exposure alkali resistance and post-exposure alkali solubility.

Furthermore, the phenolic hydroxyl-containing compound (A), represented by structural formula (1), is very rigid by virtue of the calixarene structure containing multiple naphthalene rings. The resulting permanent resist films are therefore superior in thermal decomposition resistance.

The number n in structural formula (1) is the total number of repeats and is an integer of 2 to 10. It is particularly preferred that the number n be 2, 3, 4, 5, 6, or 8, 4 in particular. This makes the phenolic hydroxyl-containing compound superior in structural stability and thermal decomposition resistance.

In structural formula (1), the two hydroxyl groups in the naphthylene structure may exist in either of the two aromatic rings of the naphthylene structure. It is preferred that the two hydroxyl groups substituting the naphthylene structure be located in positions 1 and 4, 1 and 5, 1 and 6, 2 and 6, or 2 and 7. For such a compound, raw materials are readily available. More preferably, the two hydroxyl groups are in positions 1 and 6. Such a compound is easier to produce than the others. That is, it is more preferred that the phenolic hydroxyl-containing compound (A) have a molecular structure represented by structural formula (1-1) than otherwise:

[Chem. 3]

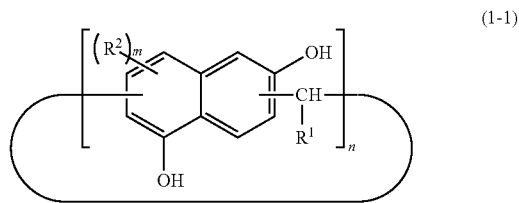

(1-1)

(where $R^2$ is hydrogen, alkyl, or aryl, and n is an integer of 2 to 10; $R^2$ is alkyl, alkoxy, aryl, aralkyl, or halogen, and m is an integer of 0 to 4; if m is 2 or more, the plurality of $R^2$s may be the same or different from one another, and may be bonded to either of the two aromatic rings in the naphthylene structure).

$R^1$ in structural formula (1) is hydrogen, alkyl, or aryl. Examples of alkyls include methyl, ethyl, propyl, butyl, pentyl, hexyl, and cyclohexyl. Examples of aryls include structural portions represented by structural formula (2-1) or (2-2):

[Chem. 4]

(2-1)

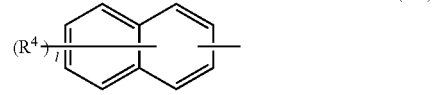

(2-2)

(where $R^3$ and $R^4$ are each independently hydroxyl, halogen, alkyl, alkoxy, aryl, or aralkyl, k is an integer of 0 to 5, and l is an integer of to 7; and if k or l is 2 or more, the plurality of $R^3$s or $R^4$s may be the same or different from one another). Specific examples include phenyl, hydroxyphenyl, dihydroxyphenyl, hydroxyalkoxyphenyl, alkoxyphenyl, tolyl, xylyl, naphthyl, hydroxynaphthyl, and dihydroxynaphthyl.

It is particularly preferred that $R^1$ be aryl. With such a compound, the curable composition gives permanent resist films that have high sensitivity, resolution, and thermal decomposition resistance. $R^1$ is more preferably a hydroxyl-containing structural portion, such as hydroxyphenyl, dihydroxyphenyl, hydroxyalkoxyphenyl, hydroxynaphthyl, or dihydroxynaphthyl.

$R^2$ in structural formula (1) is alkyl, alkoxy, aryl, aralkyl, or halogen. Examples of alkyls include methyl, ethyl, propyl, butyl, pentyl, hexyl, and cyclohexyl, and examples of alkoxys include methoxy, ethoxy, propyloxy, butoxy, pentyloxy, hexyloxy, and cyclohexyloxy. Examples of aryls include phenyl, hydroxyphenyl, dihydroxyphenyl, hydroxyalkoxyphenyl, alkoxyphenyl, tolyl, xylyl, naphthyl, hydroxynaphthyl, and dihydroxynaphthyl, and examples of aralkyls include phenylmethyl, hydroxyphenylmethyl, dihydroxyphenylmethyl, tolylmethyl, xylylmethyl, naphthylmethyl, hydroxynaphthylmethyl, dihydroxynaphthylmethyl, phenylethyl, hydroxyphenylethyl, dihydroxyphenylethyl, tolylethyl, xylylethyl, naphthylethyl, hydroxynaphthylethyl, and dihydroxynaphthylethyl.

The value of m in structural formula (1) is preferably 0. With such a compound, the curable composition gives permanent resist films superior in thermal decomposition resistance.

The phenolic hydroxyl-containing compound (A) can be produced by, for example, reacting a dihydroxynaphthalene compound with formaldehyde in the presence of a basic catalyst (method 1) or reacting a dihydroxynaphthalene compound with an aliphatic aldehyde compound having two or more carbon atoms or an aromatic aldehyde compound in the presence of an acidic catalyst (method 2). In producing the phenolic hydroxyl-containing compound by any such method, the manufacturer can optionally modify reaction conditions to selectively obtain the phenolic hydroxyl-containing compound (A) used in the present invention or to make a phenolic resin composition containing any other component. It is also possible to isolate the phenolic hydroxyl-containing compound (A) from the phenolic resin composition containing any other component.

The following describes method 1. The dihydroxynaphthalene compound used in method 1 can be, for example, 1,4-dihydroxynaphthalene, 1,5-dihydroxynaphthalene, 1,6-dihydroxynaphthalene, 2,6-dihydroxynaphthalene, 2,7-dihydroxynaphthalene, or a derivative thereof whose aromatic nucleus is substituted with one or more alkyl and/or alkoxy groups. Examples of alkyls include methyl, ethyl, propyl, butyl, pentyl, hexyl, and cyclohexyl, and examples of alkoxys include methoxy, ethoxy, propyloxy, butoxy, pentyloxy, hexyloxy, and cyclohexyloxy. These may be used individually or in combinations of two or more.

Of these dihydroxynaphthalene compounds, 1,6-dihydroxynaphthalene and derivatives thereof whose aromatic nucleus is substituted with one or more alkyl and/or aralkyl groups are particularly preferred. With such a dihydroxynaphthalene compound, the phenolic hydroxyl-containing compound forms efficiently. 1,6-Dihydroxynaphthalene is more preferred than derivatives.

The formaldehyde used in method 1 can be in the form of a solution, i.e., formalin, or a solid, i.e., paraformaldehyde.

The proportion of the dihydroxynaphthalene compound to formaldehyde in the reaction is preferably, as a molar ratio between the two reactants [(dihydroxynaphthalene compound)/(formaldehyde)], between 1.0 and 0.1. This ensures the phenolic hydroxyl-containing compound (A) forms efficiently.

The basic catalyst used in method 1 can be, for example, an alkali metal hydroxide, such as sodium hydroxide, lithium hydroxide, or potassium hydroxide, or an alkaline earth metal hydroxide, such as calcium hydroxide. It is particularly preferred that the basic catalyst be an alkali metal hydroxide because of its catalytic potential higher than that of alkaline earth metal hydroxides, more preferably sodium hydroxide. The amount of the basic catalyst is preferably between 0.02 and 1.00 mole per mole of the dihydroxynaphthalene compound.

The temperature at which the dihydroxynaphthalene compound is reacted with formaldehyde is preferably between 60° C. and 90° C. At these temperatures, the phenolic hydroxyl-containing compound forms efficiently.

The reaction of the dihydroxynaphthalene compound with formaldehyde may optionally be carried out in an organic solvent. Examples of organic solvents used include alcohol solvents such as propanol, butanol, ethylene glycol, glycerol, ethylene glycol monomethyl ether, ethylene glycol monoethyl ether, ethylene glycol monobutyl ether, and propylene glycol monomethyl ether and ester solvents such as butyl acetate, ethylene glycol monomethyl ether acetate, ethylene glycol monoethyl ether acetate, and propylene glycol monomethyl ether acetate.

The reaction of the dihydroxynaphthalene compound with formaldehyde is followed by neutralization of the system with an acidic compound. The neutralized system is cooled, and the resulting crystals of the composition are filtered out. The crystals are washed with water and dried, giving a phenolic resin composition that contains the phenolic hydroxyl-containing compound. The phenolic hydroxyl-containing compound can be obtained with a higher purity by, for example, dissolving the phenolic resin once again, in one of the aforementioned alcohol solvents or any other solvent, and adding the resulting solution dropwise to water for reprecipitation.

The following describes method 2. The dihydroxynaphthalene compound used in method 2 can be, for example, any of those dihydroxynaphthalene compounds that can be used in process 1. These may be used individually or in combinations of two or more.

Of these dihydroxynaphthalene compounds, 1,6-dihydroxynaphthalene and derivatives thereof whose aromatic nucleus is substituted with two or multiple alkyl and/or aralkyl groups are particularly preferred. With such a dihydroxynaphthalene compound, the phenolic hydroxyl-containing compound forms efficiently. 1,6-Dihydroxynaphthalene is more preferred than derivatives.

The aliphatic aldehyde compound having two or more carbon atoms or aromatic aldehyde compound used in method 2 can be, for example, a compound represented by any of structural formulae (3-1) to (3-3):

[Chem. 5]

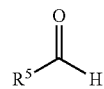
(3-1)

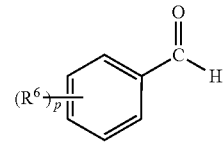
(3-2)

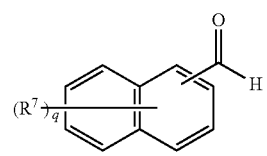
(3-3)

(where $R^5$ is a hydrocarbon having one to six carbon atoms or a structural portion resulting from replacing one or more carbon atoms in such a hydrocarbon with a hydroxyl, alkoxy, or aryl group or halogen atom; $R^6$ and $R^7$ are each independently hydroxyl, alkyl, alkoxy, aryl, aralkyl, or halogen, p is an integer of 0 to 5, and q is an integer of 0 to 7; if p or q is 2 or more, the plurality of $R^4$s or $R^5$s may be the same or different from one another).

Examples of aliphatic aldehyde compounds represented by structural formula (3-1) include acetaldehyde, propylaldehyde, butylaldehyde, isobutylaldehyde, pentylaldehyde, and hexylaldehyde.

Examples of aromatic aldehyde compounds represented by structural formula (3-2) or (3-3) include hydroxybenzaldehyde compounds such as salicylaldehyde, 3-hydroxybenzaldehyde, 4-hydroxybenzaldehyde, 2-hydroxy-4-methylbenzaldehyde, 2,4-dihydroxybenzaldehyde, and 3,4-dihydroxybenzaldehyde; hydroxy- and alkoxy-bearing benzaldehyde compounds such as 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, and 4-hydroxy-3,5-dimethoxybenzaldehyde; alkoxybenzaldehyde compounds such as methoxybenzaldehyde and ethoxybenzaldehyde; and hydroxynaphthaldehyde compounds such as 1-hydroxy-2-naphthaldehyde, 2-hydroxy-1-naphthaldehyde, and 6-hydroxy-2-naphthaldehyde. These aldehyde compounds may be used individually or in combinations of two or more.

In particular, aromatic aldehyde compounds represented by structural formula (3-2) or (3-3) are preferred. With any such aldehyde, the resulting curable composition will be highly soluble in organic solvents and give permanent resist films highly resistant to heat and superior in sensitivity. Compounds that have one or more hydroxyl groups substituting the aromatic ring(s) are more preferred. That is, it is more preferred that in structural formula (3-2) or (3-3), p or q be 1 or more with the $R^6$ or $R^7$, or at least one of the $R^6$s or $R^7$s, being hydroxy. Hydroxybenzaldehyde compounds represented by structural formula (3-2) in which p is 1 or more with the R6, or at least one of the R6s, being hydroxyl are also preferred. With such a hydroxybenzaldehyde compound, the phenolic hydroxyl-containing compound forms efficiently. It is more preferred that the aldehyde compound be any of 4-hydroxy-3-methoxybenzaldehyde, 3-ethoxy-4-hydroxybenzaldehyde, salicylaldehyde, 3-hydroxybenzaldehyde, 4-hydroxybenzaldehyde, and 2,4-dihydroxybenzaldehyde, more preferably any of salicylaldehyde, 3-hydroxybenzaldehyde, and 4-hydroxybenzaldehyde, even more preferably 4-hydroxybenzaldehyde or salicylaldehyde.

In method 2, the proportion of the dihydroxynaphthalene compound to the aldehyde compound in the reaction is preferably, as a molar ratio between the two reactants [(dihydroxynaphthalene compound)/(aldehyde compound)], between 0.1 and 3.0. This ensures the phenolic hydroxyl-containing compound forms efficiently.

The acid catalyst used in method 2 can be, for example, an inorganic acid, such as hydrochloric acid, sulfuric acid, or phosphoric acid, an organic acid, such as methanesulfonic acid, p-toluenesulfonic acid, or oxalic acid, or a Lewis acid, such as boron trifluoride, anhydrous aluminum chloride, or zinc chloride. The amount of the acid catalyst is preferably between 0.1% and 25% by mass based on the total mass of the reactants.

The temperature at which the dihydroxynaphthalene compound is reacted with the aldehyde compound is preferably between 50° C. and 120° C. At these temperatures, the phenolic hydroxyl-containing compound forms efficiently.

The reaction of the dihydroxynaphthalene compound with the aldehyde compound may optionally be carried out in an organic solvent. The organic solvent can be, for example, any of those organic solvents that can be used in process 1.

The reaction of the dihydroxynaphthalene compound with the aldehyde compound is followed by water washing of the reaction mixture. The washed mixture is dried by removing the organic solvent, with heating under reduced pressure for example, giving a composition that contains the phenolic hydroxyl-containing compound (A). The phenolic hydroxyl-containing compound can be obtained with a higher purity by, for example, dissolving the composition once again, in one of the aforementioned alcohol solvents or any other solvent, and adding the resulting solution dropwise to water for reprecipitation.

Such phenolic hydroxyl-containing compounds used in the present invention, highly soluble in commonly used organic solvents and capable of giving coatings superior in thermal decomposition resistance as described above, are suitable for use in permanent resist film applications, and can also be used in various electrical and electronic component applications other than permanent resist films, such as adhesives, paints, photoresists, and printed circuit boards. Furthermore, the phenolic hydroxyl-containing compounds used in the present invention can potentially be applied to, for example, qualitative or quantitative analysis of metal ions, separation of metal ions, molecular sensors, artificial enzymes, materials for different chromatographic techniques, and charge controlling agents for toners, by virtue of their clathrating and catalytic functions derived from the structure.

A curable composition according to the present invention for permanent resist films contains, as noted above, a phenolic hydroxyl-containing compound (A) and a photosensitizer (B1) or curing agent (B2).

The photosensitizer (B1) used in the present invention can be, for example, a quinonediazide-bearing compound. Specific examples of quinonediazide-bearing compounds include complete esters, partial esters, amides, and partial amides of aromatic (poly)hydroxy compounds with quinonediazide-bearing sulfonic acids, such as naphthoquinone-1,2-diazide-5-sulfonic acid, naphthoquinone-1,2-diazide-4-sulfonic acid, and ortho-anthraquinone diazide sulfonic acid.

Examples of aromatic (poly)hydroxy compounds used include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-(1-[4-{2-(4-hydroxyphenyl)-2-propyl}phenyl]ethylidene)bisphenol, and 3,3'-dimethyl-(1-[4-{2-(3-methyl-4-hydroxyphenyl)-2-propyl}phenyl]ethylidene)bisphenol;

tris(hydroxyphenyl)methane compounds such as tris(4-hydroxyphenyl)methane, bis(4-hydroxy-3,5-dimethylphenyl)-4-hydroxyphenylmethane, bis(4-hydroxy-2,5-dimethylphenyl)-4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4-dihydroxyphenylmethane, and bis(4-hydroxy-3,5-dimethylphenyl)-3,4-dihydroxyphenylmethane and their methyl-substituted derivatives; and bis(cyclohexylhydroxyphenyl)(hydroxyphenyl)methane compounds such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis(5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, and bis(5-cyclohexyl-2-hydroxy-4-methylphenyl)-4-hydroxyphenylmethane and their methyl-substituted derivatives. These photosensitizers may be used individually or in combinations of two or more.

The amount of the photosensitizer(s) (B1) in the curable composition according to the present invention for permanent resist films is preferably such that the photosensitizer(s) constitutes 5 to 50 parts by mass per 100 parts by mass of the phenolic hydroxyl-containing compound (A). Such a curable composition gives permanent resist films superior in light sensitivity.

The curing agent (B2) used in the present invention can be, for example, a melamine, guanamine, glycoluril, or urea compound substituted with at least one group selected from methylol, alkoxymethyl, and acyloxymethyl, a resol resin, an epoxy compound, an isocyanate compound, an azide compound, a compound with an alkenyl-ether or other double bond, an acid anhydride, or an oxazoline compound.

Examples of melamine compounds include hexamethylolmelamine, hexamethoxymethylmelamine, hexamethylolmelamine compounds with 1 to 6 methylol groups methoxymethylated, hexamethoxyethylmelamine, hexaacyloxymethylmelamines, and hexamethylolmelamine compounds with 1 to 6 methylol groups acyloxymethylated.

Examples of guanamine compounds include tetramethylolguanamine, tetramethoxymethylguanamine, tetramethoxymethylbenzoguanamine, tetramethylolguanamine compounds with 1 to 4 methylol groups methoxymethylated, tetramethoxyethylguanamine, tetraacyloxyguanamines, and tetramethylolguanamine compounds with 1 to 4 methylol groups acyloxymethylated.

Examples of glycoluril compounds include 1,3,4,6-tetrakis(methoxymethyl)glycoluril, 1,3,4,6-tetrakis(butoxymethyl)glycoluril, and 1,3,4,6-tetrakis(hydroxymethyl)glycoluril.

Examples of urea compounds include 1,3-bis(hydroxymethyl)urea, 1,1,3,3-tetrakis(butoxymethyl)urea, and 1,1,3,3-tetrakis(methoxymethyl)urea.

Examples of resol resins include polymers resulting from an alkali-catalyzed reaction between a phenolic hydroxyl-containing compound, e.g., phenol, an alkyl phenol such as cresol or xylenol, phenylphenol, resorcinol, biphenyl, a bisphenol such as bisphenol A or bisphenol F, naphthol, or dihydroxynaphthalene, and an aldehyde compound.

Examples of epoxy compounds include tris(2,3-epoxypropyl)isocyanurate, trimethylolmethane triglycidyl ether, trimethylolpropane triglycidyl ether, and triethylolethane triglycidyl ether.

Examples of isocyanate compounds include tolylene diisocyanate, diphenylmethane diisocyanate, hexamethylene diisocyanate, and cyclohexane diisocyanate.

Examples of azide compounds include 1,1'-biphenyl-4,4'-bisazide, 4,4'-methylidenebisazide, and 4,4'-oxybisazide.

Examples of compounds with alkenyl-ether or other double bonds include ethylene glycol divinyl ether, triethylene glycol divinyl ether, 1,2-propanediol divinyl ether, 1,4-butanediol divinyl ether, tetramethylene glycol divinyl ether, neopentylglycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of acid anhydrides include aromatic acid anhydrides such as phthalic anhydride, trimellitic anhydride, pyromellitic anhydride, 3,3',4,4'-benzophenonetetracarboxylic dianhydride, biphenyltetracarboxylic dianhydride, 4,4'-(isopropylidene)diphthalic anhydride, and 4,4'-(hexafluoroisopropylidene)diphthalic anhydride; and alicyclic carboxylic anhydrides such as tetrahydrophthalic anhydride, methyltetrahydrophthalic anhydride, hexahydrophthalic anhydride, methylhexahydrophthalic anhydride, endomethylenetetrahydrophthalic anhydride dodecenylsuccinic anhydride, and trialkyltetrahydrophthalic anhydrides.

Of these, glycoluril compounds, urea compounds, and resol resins are particularly preferred. With these highly effective curing agents, the curable composition gives permanent resist films superior in thermal decomposition resistance. In particular, glycoluril compounds are preferred.

The amount of the curing agent (B2) in the curable composition according to the present invention is preferably such that the curing agent constitutes 0.5 to 20 parts by mass per 100 parts by mass of the phenolic hydroxyl-containing compound (A). This makes the composition superior in curability.

The curable composition according to the present invention for permanent resist films may contain any other resin (A') in combination with the phenolic hydroxyl-containing compound (A). The optional resin (A') can be any resin that is soluble in alkali developers by itself or dissolves in alkali developers when used in combination with additives such as an acid generator.

The optional resin (A') can be, for example, (A'-1) any phenolic resin other than the phenolic hydroxyl-containing compound (A); (A'-2) a homopolymers or copolymer of p-hydroxystyrene, p-(1,1,1,3,3,3-hexafluoro-2-hydroxypropyl)styrene or any other hydroxy-containing styrene; (A'-3) a derivative resulting from altering the hydroxyl groups of (A'-1) or (A'-2) with t-butoxycarbonyl, benzyloxycarbonyl, or any other acid-decomposing group; (A'-4) a homopolymers or copolymer of (meth)acrylic acid; or (A'-5) an alternating copolymer of an alicyclic polymerizable monomer, such as a norbornene or tetracyclodecene compound, with maleic anhydride or male imide.

For such optional resins (A'), examples of optional phenolic resins (A'-1) include phenolic resins such as phenol novolac resins, cresol novolac resins, naphthol novolac resins, co-condensed novolac resins made from several phenolic compounds, phenolic resins modified with aromatic hydrocarbon formaldehyde resins, resins of dicyclopentadiene phenol adduct type, phenol aralkyl resins (Xylok resins), naphthol aralkyl resins, trimethylolmethane resins, tetraphenylolethane resins, biphenyl-modified phenolic resins (polyphenolic compounds in which bis-methylene group(s) connects phenolic nuclei), biphenyl-modified naphthol resins (polynaphthol compounds in which bis-methylene group(s) connects phenolic nuclei), aminotriazine-modified phenolic resins (polyphenolic compounds in which melamine, benzoguanamine, or any similar species connects phenolic nuclei), and novolac resins modified with alkoxy-containing aromatic rings (polyphenolic compounds in which formaldehyde connects phenolic nuclei and alkoxy-containing aromatic rings).

Of these optional phenolic resins (A'), cresol novolac resins and co-condensed novolac resins made from cresol and other phenolic compounds are particularly preferred. These resins make the permanent resist films made from the curable composition highly sensitive and superior in heat resistance. The cresol novolac resins and co-condensed novolac resins made from cresol and other phenolic compounds are, specifically, novolac resins made essentially from at least one cresol selected from the group consisting of o-cresol, m-cresol, and p-cresol and an aldehyde compound, optionally with other phenolic compounds.

Examples of optional, or non-cresol, phenolic compounds include phenol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as p-phenylphenol, aminophenol, nitrophenol, dinitrophenol, and trinitrophenol; fused polycyclic phenols such as 1-naphthol and 2-naphthol; and polyphenols such as resorcinol, alkylresorcinols, pyrogallol, catechol, alkylcatechols, hydroquinone, alkylhydroquinones, phloroglucinol, bisphenol A, bisphenol F, bisphenol S, and dihydroxynaphthalene. These optional phenolic compounds may be used individually or in combinations of two or more. When optional phenolic compound(s) is used, the amount thereof is preferably between 0.05 and 1 mole per mole based on the total number of moles of the starting cresol(s).

Examples of aldehyde compounds include formaldehyde, paraformaldehyde, trioxane, acetaldehyde, propionaldehyde, polyoxymethylene, chloral, hexamethylenetetramine, furfural, glyoxal, n-butyraldehyde, caproaldehyde, allylaldehyde, benzaldehyde, crotonaldehyde, acrolein, tetraoxymethylene, phenylacetaldehyde, o-tolualdehyde, and salicylaldehyde. These aldehyde compounds may be used individually or in combinations of two or more. Formaldehyde is particularly preferred because of its superior reactivity and can be used in combination with other aldehyde compounds. If formaldehyde is used in combination with any other aldehyde compound, it is preferred that the amount of the additional aldehyde compound be between 0.05 and 1 mole per mole of formaldehyde.

In producing the novolac resin, the ratio of aldehyde compounds to phenolic compounds in the reaction is preferably in the range of 0.3 to 1.6 moles, more preferably 0.5 to 1.3, of aldehyde compounds per mole of phenolic compounds. This makes the photosensitive resin composition superior in sensitivity and heat resistance.

In an exemplary method, the phenolic compound is reacted with the aldehyde compound at a temperature of 60° C. to 140° C. in the presence of an acid catalyst, and then water and any residual monomers are removed under reduced pressure. Examples of acid catalysts used include oxalic acid, sulfuric acid, hydrochloric acid, phenolsulfonic acid, para-toluene sulfonic acid, zinc acetate, and manganese acetate. These acid catalysts may be used individually or in combinations of two or more. Oxalic acid is particularly preferred because of its superior catalytic activity.

Of such cresol novolac resins and co-condensed novolac resins made from cresol and other phenolic compounds, particularly preferred cresol novolac resins are made using meta-cresol alone or meta-cresol and para-cresol in combination. For the latter, the molar ratio between meta-cresol and para-cresol in the reaction [meta-cresol/para-cresol] is preferably between 10/0 and 2/8, more preferably between 7/3 and 2/8. This leads to a good balance between the sensitivity and heat resistance of the photosensitive resin composition.

When an optional resin (A') is used, the proportions of the phenolic hydroxyl-containing compound (A) and the optional resin (A') is preferably such that the phenolic hydroxyl-containing compound (A) content is 60% by mass or more based on the total amount of resin components, more preferably 80% by mass or more. Such a curable composition gives permanent resist films highly sensitive to light and superior in resolution and heat resistance.

When an optional resin (A') is used, the amount of the photosensitizer(s) (B1) in the curable composition according to the present invention is preferably such that the photosensitizer(s) constitutes 5 to 50 parts by mass per 100 parts by mass based on the total amount of resin components in the composition. Such a curable composition gives permanent resist films superior in light sensitivity.

The curable composition according to the present invention may contain a surfactant for purposes such as improved film formation properties, better pattern adhesion, and reduced occurrence of development defects in the creation of permanent resist films. Examples of surfactants used include nonionic surfactants, e.g., polyoxyethylene alkyl ether compounds such as polyoxyethylene lauryl ether, polyoxyethylene stearyl ether, polyoxyethylene cetyl ether, and polyoxyethylene oleyl ether, polyoxyethylene alkylallyl ethers such as polyoxyethylene octylphenol ether and polyoxyethylene nonylphenol ether, polyoxyethylene-polyoxypropylene block copolymers, sorbitan fatty acid ester compounds such as sorbitan monolaurate, sorbitan monopalmitate, sorbitan monostearate, sorbitan monooleate, sorbitan trioleate, and sorbitan tristearate, and polyoxyethylene sorbitan fatty acid ester compounds such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorosurfactants, i.e., surfactants that have fluorine atoms in their molecular structure, such as copolymers of fluoroaliphatic-bearing polymerizable monomers with [poly(oxyalkylene)](meth)acrylate; and silicone surfactants, i.e., surfactants that have a silicone structural portion in their molecular structure. These may be used individually or in combinations of two or more.

The amount of the surfactant(s) is preferably between 0.001 and 2 parts by mass per 100 parts by mass of solid resin in the curable composition according to the present invention.

The curable composition according to the present invention can be obtained as a solution in an organic solvent optionally containing other resins (A') and/or additives such as surfactants, dyes, fillers, crosslinking agents, and dissolution aids.

Examples of organic solvents include alkylene glycol monoalkyl ethers such as ethylene glycol monomethyl ether, ethylene glycol monoethyl ether, ethylene glycol monopropyl ether, ethylene glycol monobutyl ether propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; alkylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These may be used individually or in combinations of two or more.

The curable composition according to the present invention may contain any resin other than the phenolic hydroxyl-containing compound (A) and phenolic resins (A') unless the advantages of the present invention are lost. Examples of optional resins used include novolac resins, resins resulting from addition polymerization of an alicyclic diene compound, such as dicyclopentadiene, with a phenolic compound, modified novolac resins made from a phenolic hydroxyl-containing compound and an alkoxy-containing aromatic compound, phenol aralkyl resins (Xylok resins), naphthol aralkyl resins, trimethylolmethane resins, tetraphenylolethane resins, biphenyl-modified phenolic resins, biphenyl-modified naphthol resins, aminotriazine-modified phenolic resins, and vinyl polymers.

More specific examples of novolac resins include polymers resulting from an acid-catalyzed reaction between a phenolic hydroxyl-containing compound, e.g., phenolenol, an alkyl phenol such as cresol or xylenol, phenylphenol, resorcinol, biphenyl, a bisphenol such as bisphenol A or bisphenol F, naphthol, or dihydroxynaphthalene and an aldehyde compound.

Examples of vinyl polymers include homopolymers and copolymers of vinyl compounds such as polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, and poly(meta)acrylate.

When an optional resin is used, the proportions of the phenolic hydroxyl-containing compound (A) and the optional resin can be adjusted according to the intended purpose of use. Preferably, the proportions are such that the optional resin constitutes 0.5 to 100 parts by mass per 100 parts by mass of the phenolic hydroxyl-containing compound (A). This makes the advantage of the present invention of superior thermal decomposition resistance of permanent resist films more significant.

When an optional resin is used, furthermore, the amount of the curing agent (B2) in the curable composition according to the present invention is preferably such that the curing agent constitutes 0.5 to 50 parts by mass per 100 parts by mass based on the total amount the phenolic hydroxyl-containing compound (A) and the optional resin. This makes the composition superior in curability.

The curable composition according to the present invention for permanent resist films can be conditioned by combining its components, described above, and mixing them using, for example, a mixer. If the curable composition for permanent resist films contains fillers and/or pigments, it can be conditioned through dispersion or mixing using a dispersing machine, such as a dissolver, a homogenizer, or a three-roll mill.

In an exemplary photolithographic process that uses a curable composition according to the present invention for permanent films, a solution or dispersion of the photosensitive composition for permanent films in an organic solvent is applied to the subject of the photolithography a silicon substrate and prebaked at a temperature of 60° C. to 150° C. Any coating technique can be used, such as spin coating, roll coating, flow coating, dip coating, spray coating, and doctor blading. A resist pattern is then created. When the photosensitive composition for permanent films is a positive one, the desired resist pattern is exposed to light through a predetermined mask, and an alkali developer is applied to dissolve the exposed parts, forming the resist pattern. By virtue of its high light sensitivity, the photosensitive composition according to the present invention for permanent films can be formed into resist patterns superior in resolution.

Thin films made through the application of a curable composition according to the present invention for permanent films (coatings or permanent resist films) are suitable for use as permanent films, films that remain in finished products optionally with prior formation of resist patterns. Specific examples of permanent films related to semiconductor devices include solder resists, packaging material, underfill, package bonding layers for circuit devices or other components, and layers for bonding integrated circuit devices to a circuit board. Specific examples of permanent films related to thin displays, typified by LCDs and OELDs, include protective coatings for thin-film transistors, protective coatings for liquid-crystal color filters, black matrix, and spacers. Besides being superior in heat resistance and moisture absorption resistance, permanent films made from a photosensitive composition according to the present invention for permanent films offer the outstanding advantage of low contamination in particular, because they release only traces of hydroxynaphthalenes. Of particular importance is therefore that in producing display materials, the manufacturer can minimize the degradation of image quality associated with contamination, which is serious for display materials, by forming permanent films from a photosensitive composition according to the present invention for permanent films. The photosensitive composition according to the present invention for permanent films is therefore a material with little risk of image quality degradation that combines high sensitivity, high heat resistance, and hygroscopic reliability.

EXAMPLES

The following specifically describes the present invention by providing examples and comparative examples. In the following, "parts" and "%" are by mass unless otherwise specified. The measurement conditions for GPC, 1H-NMR, IR, and FD-MS spectrometry were as follows.

<GPC Conditions>
Instrument: Tosoh Corporation "HLC-8220 GPC"
Columns: Tosoh Corporation "HHR-H" guard column (6.0 mm I.D.×4 cm)+Tosoh Corporation "TSK-GEL GMHHR-N" (7.8 mm I.D.×30 cm)+Tosoh Corporation "TSK-GEL GMHHR-N" (7.8 mm I.D.×30 cm)+Tosoh Corporation "TSK-GEL GMHHR-N" (7.8 mm I.D.×30 cm)+ Tosoh Corporation "TSK-GEL GMHHR-N" (7.8 mm I.D.× 30 cm)

Detector: ELSD (Alltech Japan K.K. "ELSD 2000")
Data processing: Tosoh Corporation "GPC-8020 Model II Data Analysis Version 4.30"
Measurement conditions: Column temperature 40° C.
Developing solvent Tetrahydrofuran (THF)
Flow rate 1.0 ml/min
Sample: A solution of 1.0% by mass resin, on a solid basis, in tetrahydrofuran filtered through a microfilter (5 μl)
Standard samples: As directed in the measurement manual for "GPC-8020 Model II Data Analysis Version 4.30," the below listed monodisperse polystyrenes, with known molecular weights, were used.
(Monodisperse Polystyrenes)
  Tosoh Corporation "A-500"
  Tosoh Corporation "A-1000"
  Tosoh Corporation "A-2500"
  Tosoh Corporation "A-5000"
  Tosoh Corporation "F-1"
  Tosoh Corporation "F-2"
  Tosoh Corporation "F-4"
  Tosoh Corporation "F-10"
  Tosoh Corporation "F-20"
  Tosoh Corporation "F-40"
  Tosoh Corporation "F-80"
  Tosoh Corporation "F-128"
  Tosoh Corporation "F-288"
  Tosoh Corporation "F-550"
<$^1$H-NMR Conditions>
  Instrument: JEOL Ltd. AL-400
  Solvent: Dimethylsulfoxide-d6 with reference TMS
  Sample concentration: 30 wt %
  Measurement mode: SGNNE (NOE suppression with complete 1H decoupling)
  Pulse angle: 45° pulses
  Number of scans: 10000
<IR Spectrometry Conditions>
  Measurements were taken by the KBr pellet technique using JASCO Corporation "FT/IR-500."
<FD-MS Spectrometry Conditions>
  Measurements were taken using JEOL Ltd. AX505H (FD505H) double-focusing mass spectrometer.

Synthesis Example 1 [Synthesis of a Phenolic Hydroxyl-Containing Compound (A)]

A flask fitted with a thermometer, a dropping funnel, a condenser, and a stirrer was charged with 160 g of 1,6-dihydroxynaphthalene, 122 g of 4-hydroxybenzaldehyde, 290 g of 2-ethoxyethanol, and 1.7 g of 95% sulfuric acid. After heating to 80° C., the ingredients were stirred for 8 hours. After the completion of the reaction, 300 g of ethyl acetate and 160 g of ion-exchanged water were added. In a separatory funnel, the aqueous layer, which was the lower layer and had a pH of 1, was released. The organic layer was washed with 160 g of ion-exchanged water seven times, and the released aqueous layers were checked to ensure that the pH was 4. The organic layer, or the upper layer, was concentrated by heating under reduced pressure using an evaporator. The residue was further dried, giving 247 g of a composition containing 89%, based on area ratios in GPC, of the intended phenolic hydroxyl-containing compound (A1). The yield was 93%, and an FD-MS spectrum had a peak at 1056 indicating the presence of a cyclic compound [a compound having a molecular structure represented by structural formula (1)).

Figure 2:
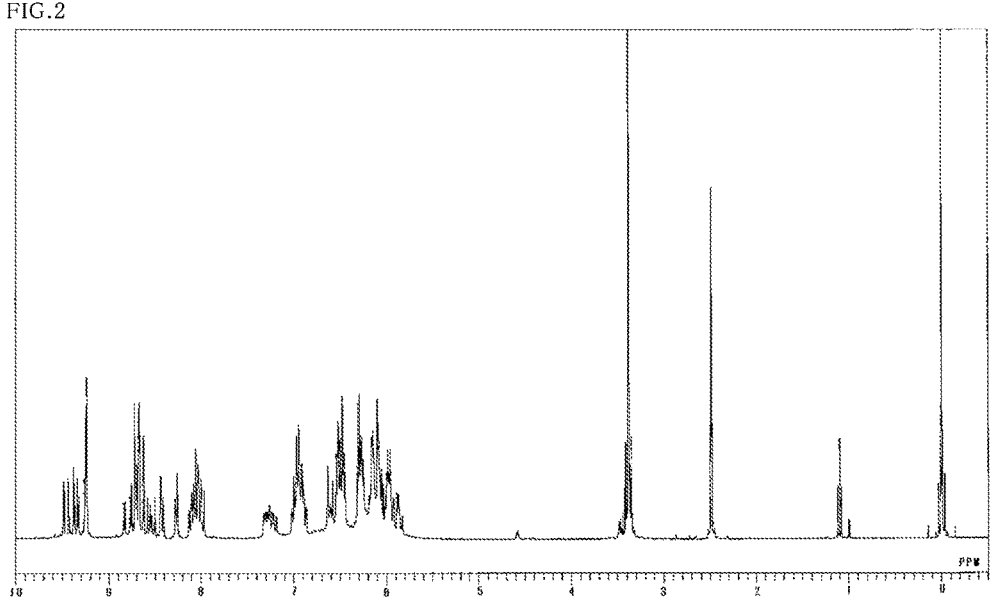
FIG. 2 is a 1H-NMR chart of phenolic hydroxyl-containing compound (A1), obtained in Synthesis Example 1.
Figure 3:
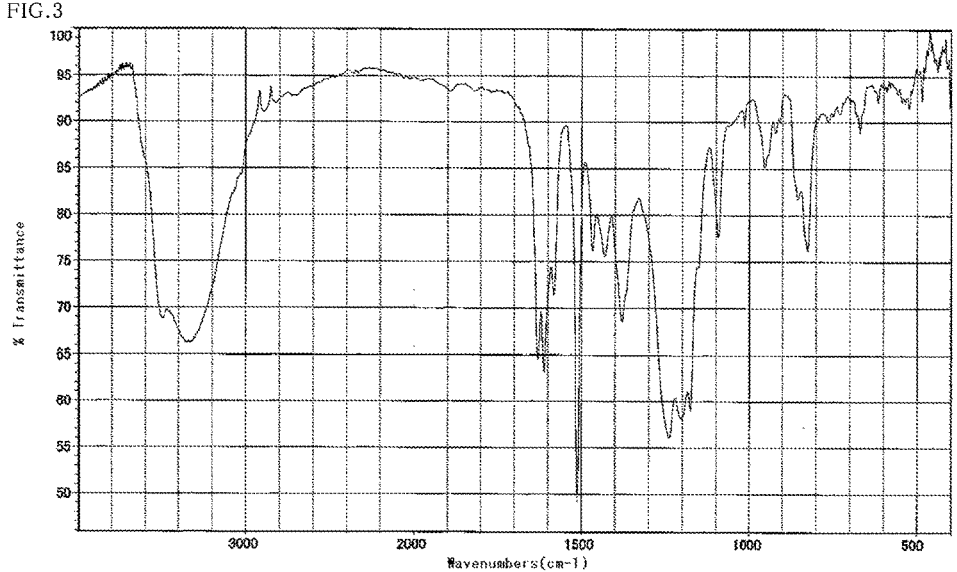
FIG. 3 is an IR chart of phenolic hydroxyl-containing compound (A1), obtained in Synthesis Example 1.
Figure 4:
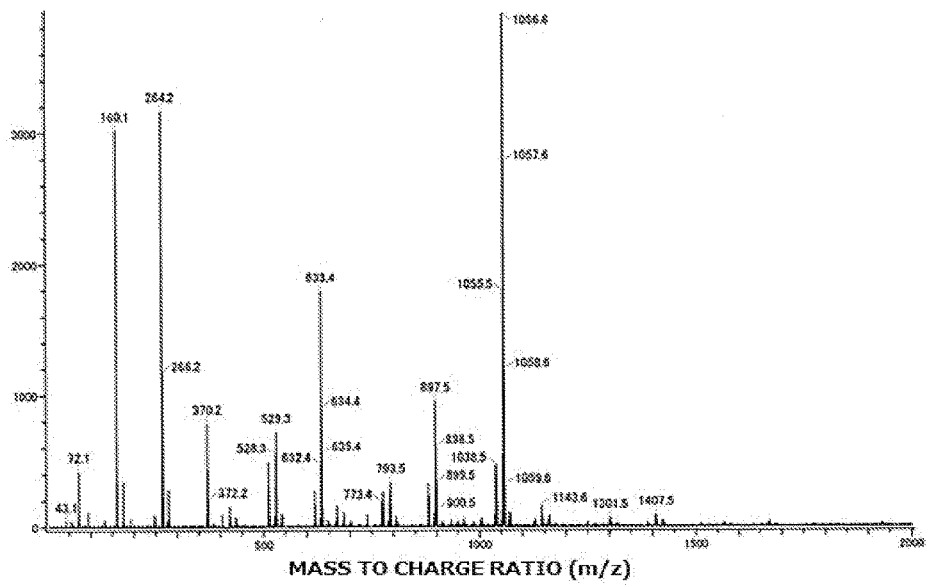
FIG. 4 is an FD-MS chart of phenolic hydroxyl-containing compound (A1), obtained in Synthesis Example 1.

A solution of 20 g of the composition, containing 89% phenolic hydroxyl-containing compound (A1) based on area ratios in GPC, in 20 g of methanol was added dropwise to 60 g of ion-exchanged water with stirring so that reprecipitation would occur. The formed precipitate was collected through filtration and dried using a vacuum dryer, giving 12 g of the intended phenolic hydroxyl-containing compound (A1). FIGS. 1, 2, 3, and 4 are GPC, $^1$H-NMR, IR, and FD-MS charts, respectively, of the phenolic hydroxyl-containing compound (A1). The phenolic hydroxyl-containing compound (A1), corresponding to the peak at 1156 detected in the FD-MS spectrum, had the structure illustrated below.

[Chem. 6]

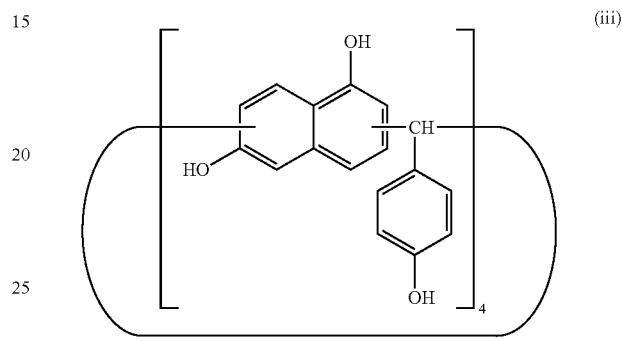

(iii)

Synthesis Example 2 (Same as Above)

The procedure of Synthesis Example 1 was repeated with 122 g of salicylaldehyde instead of 122 g of 4-hydroxybenzaldehyde, yielding 252 g of a composition containing 95% phenolic hydroxyl-containing compound (A2) based on area ratios in GPC. An FD-MS spectrum had a peak at 1056 indicating the presence of a cyclic compound [a compound having a molecular structure represented by structural formula (1)).

Figure 5:
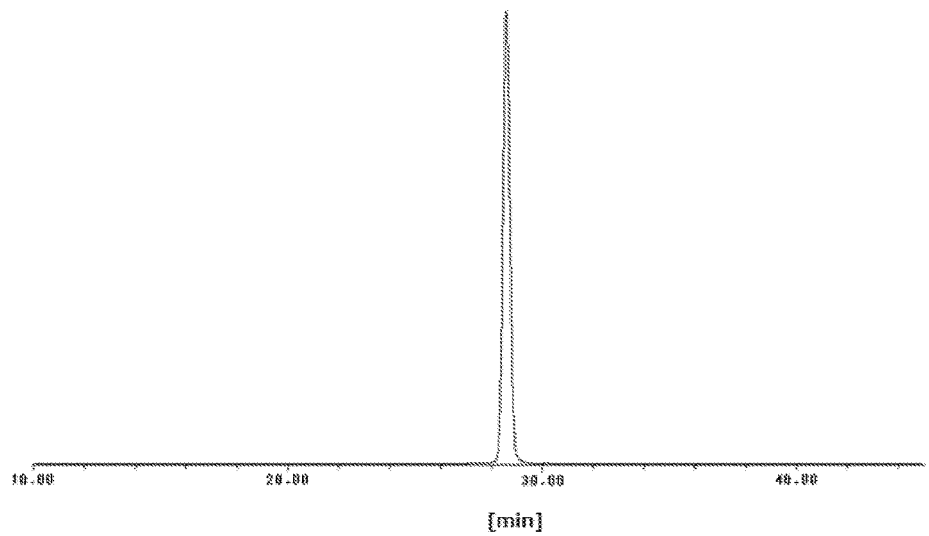
FIG. 5 is a GPC chart of phenolic hydroxyl-containing compound (A2), obtained in Synthesis Example 2.
Figure 6:
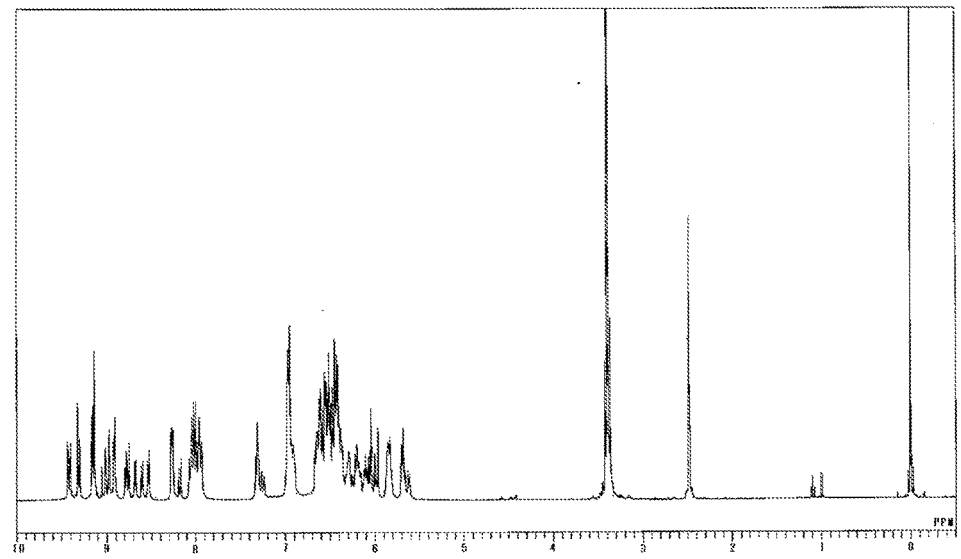
FIG. 6 is a 1H-NMR chart of phenolic hydroxyl-containing compound (A2), obtained in Synthesis Example 2.
Figure 7:
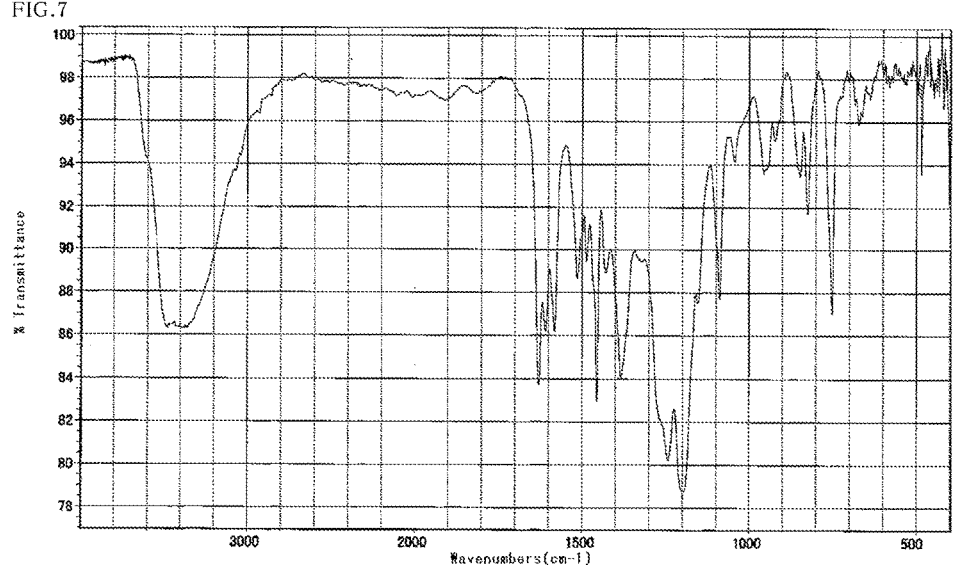
FIG. 7 is an IR chart of phenolic hydroxyl-containing compound (A2), obtained in Synthesis Example 2.
Figure 8:
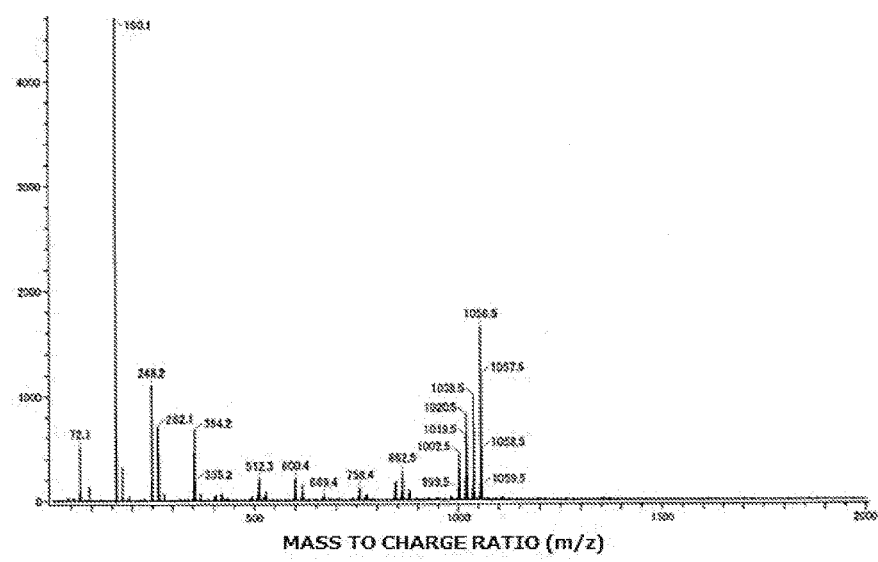
FIG. 8 is an FD-MS chart of phenolic hydroxyl-containing compound (A2), obtained in Synthesis Example 2.

The operation for reprecipitation in Synthesis Example 1 was performed with 20 g of the composition containing 95% phenolic hydroxyl-containing compound (A2) based on area ratios in GPC, giving 12 g of the intended phenolic hydroxyl-containing compound (A2). FIGS. 5, 6, 7, and 8 are GPC, $^1$H-NMR, IR, and FD-MS charts, respectively, of the phenolic hydroxyl-containing compound (A2). The phenolic hydroxyl-containing compound (A2), corresponding to the peak at 1156 detected in the FD-MS spectrum, had the structure illustrated below.

[Chem. 7]

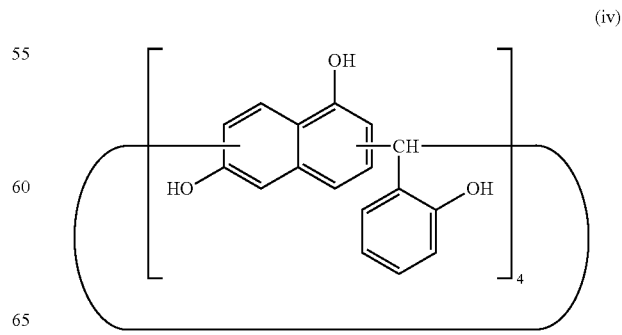

(iv)

Synthesis Example 3 (Synthesis of a Comparative Cyclic Compound)

A flask fitted with a thermometer, a dropping funnel, a condenser, and a stirrer was charged with 48 g (0.30 moles) of α-naphthol, 26 g (0.36 moles) of a 42% aqueous solution of formaldehyde, 50 g of isopropyl alcohol, and 9.4 g (0.11 moles) of a 48% sodium hydroxide, and the ingredients were stirred with nitrogen purge at room temperature. The mixture was stirred for 1 hour at an increased temperature of 80° C. After the completion of the reaction, the mixture was neutralized with 8 g of monosodium phosphate. The mixture was then cooled, and the resulting crystals were filtered out. The crystals were washed with 50 g of water three times and then dried by heating under reduced pressure, giving 47 g of a comparative cyclic compound [a comparative phenolic hydroxyl-containing compound (A'1)].

Synthesis Example 4 (Synthesis of a Comparative Noncyclic Compound)

A 1-L four-neck flask fitted with a thermometer, a condenser, and a stirrer was charged with 144 g (1.0 mole) of 1-naphthol, 400 g of methyl isobutyl ketone, 96 g of water, and 27.7 g (0.85 moles) of 92% paraformaldehyde. To the flask was added 4.8 g of an aqueous solution of para-toluene sulfonic acid adjusted to a concentration of 50% with stirring. The mixture was heated to 80° C. and allowed to react for 2 hours with stirring. After the completion of the reaction, the solution in the system was transferred to a separatory funnel, and the aqueous layer was separated from the organic layer and removed. After being washed with water until the washing water became neutral, the organic layer was heated under reduced pressure to remove solvents, yielding 47 g of a comparative cyclic compound [a naphthol phenolic resin (A'2)].

Example 1

A curable composition (1) according to the present invention for permanent resist films was prepared using the phenolic hydroxyl-containing compound (A1) as described below. The solubility in solvent of the resulting curable composition (1) for permanent resist films and the developability in alkali solution, light sensitivity, and resolution of coatings made using composition (1) were evaluated by the methods specified below. Furthermore, the heat resistance of the phenolic hydroxyl-containing compound (A1) was evaluated by the method set forth below. The results are given in Table 1.

<Solubility in Solvent Testing>

Eight parts of the phenolic hydroxyl-containing compound (A1) and 2 parts of a photosensitizer (Toyo Gosei Co., Ltd. "P-200", a condensation product of 1 mole of 4,4'-[1-[4-[1-(4-hydroxyphenyl)-1-methylethyl]phenyl]ethylidene] bisphenol and 2 moles of 1,2-naphthoquinone-2-diazide-5-sulfonyl chloride) were added to propylene glycol monomethyl ether acetate (hereinafter abbreviated to "PGMEA") to make the concentration of the solution 20%, giving a curable composition (1-1) according to the present invention for permanent resist films. Curable composition (1-1) for permanent resist films was stirred using a shaker at ordinary temperature, yielding a PGMEA solution. The solution was stirred, and the solvent in the vessel was visually inspected.

Dissolved: Uniform and transparent
Not dissolved: Solids separated out or precipitated <Evaluation of the Developability of Coating in Alkali Solution>

The PGMEA solution of <Solubility in Solvent Testing> was applied to a silicon wafer 5 inches in diameter using a spin coater. The applied composition was dried at 110° C. for 60 seconds, giving a coating approximately 1 μm thick. After 60 seconds of immersion in an alkali solution (a 2.38% by mass aqueous solution of tetramethylammonium hydroxide), the thickness of the coating was measured using a film thickness measurement instrument (Filmetrics "F-20"). The alkali dissolution rate (ADR) determined from the measurement was used to assess alkali solution resistance. The ADR was determined before and after the exposure of the thin film. The exposure dose was 100 mJ/cm$^2$.

<Light Sensitivity Testing>

Sixteen parts of the phenolic hydroxyl-containing compound (A1) and 3 parts of a curing agent (Tokyo Chemical Industry Co., Ltd. "1,3,4,6-Tetrakis(methoxymethyl)glycoluril") were added to 100 parts of PGMEA. The ingredients were mixed and dissolved. The resulting solution was filtered through a 0.2-μm membrane filter, yielding a curable composition (1-2) according to the present invention for permanent resist films.

Curable composition (1-2) for permanent resist films was applied to a silicon wafer to a thickness of approximately 1 μm and dried. With this silicon wafer tightly covered with a mask compatible with 1 to 10 μm 1:1 line-and-space resist patterns, the exposure dose was determined at which a 3-μm pattern can be faithfully reproduced with a lamp emitting g-, h-, and i-lines (Eop dose). The lower this dose is, the more sensitive the coating is.

<Resolution Testing>

Curable composition (1-2) for permanent resist films was applied to a silicon wafer and dried. This silicon wafer was exposed to light at 100 mJ/cm$^2$ using Ushio Inc. Multilight (g-, h-, and i-lines) with a photomask thereon. The exposed coating was developed and dried as in <Solubility in Solvent Testing>. The resulting pattern was observed under Keyence Corporation VK-8500 laser microscope and rated for its condition against the criteria below.

○: Resolution was achieved with L/S=5 μm.
X: Resolution was not achieved with L/S=5 μm.

<Evaluation of the Heat Resistance of Phenolic Hydroxyl-Containing Compound (A1)>

The thermal decomposition temperature was determined by heating the compound at a constant rate with weight loss monitoring using a thermogravimetry/differential thermal analyzer (TG/DTA) under the conditions specified below. The higher this temperature is, the more resistant to heat the compound is.

Instrument: Seiko Instruments Inc. TG/DTA 6200
Temperature range: RT to 400° C.
Heating rate: 10° C./min
Atmosphere: Nitrogen

Example 2 and Comparative Examples 1 and 2

The procedures of Example 1 were repeated with the formulations given in Table 1, and the resulting curable composition for permanent resist films and comparative curable compositions for permanent resist films were tested as in Example 1. The results are given in Table 1.

TABLE 1

|  |  | Example 1 | Example 2 | Comparative Example 1 | Comparative Example 2 |
|---|---|---|---|---|---|
| Phenolic hydroxyl-containing compound | | (A1) | (A2) | (A'1) | (A'2) |
| Solubility in solvent | | ○ | ○ | x | ○ |
| Alkali developability [ADR (nm/sec)] | Before exposure | 0 | 0 | — | 0 |
| | After exposure | >500 | >500 | — | 113 |
| Sensitivity (mJ/cm2) | | 40 | 40 | — | 60 |
| Resolution | | ○ | ○ | — | x |
| Thermal decomposition temperature (° C.) | | >200 | >200 | >200 | >200 |

The invention claimed is:

1. A calix[2-10]arene compound which is obtained by reacting only an 1,6-dihydroxynaphthalene compound with an aromatic aldehyde as reactants in the presence of a catalyst;
wherein the 1,6-dihydroxynaphthalene is unsubstituted or substituted by any of alkyl, alkoxy, aryl, aralkyl or halogen; and
wherein the aromatic aldehyde is represented by structure

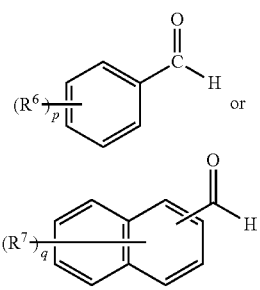

where $R^6$ and $R^7$ are each independently hydroxyl, halogen, alkyl, alkoxy, aryl, or aralkyl, p is an integer of 0 to 5, and q is an integer of 0 to 7; and if p or q is 2 or more, the plurality of $R^6$s or $R^7$s may be the same or different from one another.

2. The calix[2-10]arene compound according to claim 1, wherein the aromatic aldehyde is selected from a group consisting of salicylaldehyde, 3-hydroxybenzaldehyde, 4-hydroxybenzaldehyde, 2-hydroxy-4-methylbenzaldehyde, 2,4-dihydroxybenzaldehyde, 3,4-dihydroxybenzaldehyde, 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, 4-hydroxy-3,5-dimethoxybenzaldehyde, methoxybenzaldehyde, ethoxybenzaldehyde, 1-hydroxy-2-naphthaldehyde, 2-hydroxy-1-naphthaldehyde, 6-hydroxy-2-naphthaldehyde, or combination thereof.

3. A composition comprising the calix[2-10]arene compound according to claim 2 and a photosensitizer (B1) or curing agent (B2), wherein the composition is a curable composition.

4. A permanent resist film comprising the curable composition according to claim 3.

5. The calix[2-10]arene compound according to claim 1 is a product of reacting the 1,6-dihydroxynaphthalene compound with the aromatic aldehyde in the presence of an acidic catalyst.

6. The calix[2-10]arene compound according to claim 5, wherein the aromatic aldehyde is 4-hydroxybenzaldehyde or salicylaldehyde.

7. A composition comprising the calix[2-10]arene compound according to claim 6 and a photosensitizer (B1) or curing agent (B2), wherein the composition is a curable composition.

8. A permanent resist film comprising the curable composition according to claim 7.

9. A composition comprising the calix[2-10]arene compound according to claim 5 and a photosensitizer (B1) or curing agent (B2) wherein the composition is a curable composition.

10. A permanent resist film comprising the curable composition according to claim 9.

11. A composition comprising the calix[2-10]arene compound according to claim 1 and a photosensitizer (B1) or curing agent (B2).

12. The composition according to claim 11, wherein the photosensitizer (B1) constitutes 5 to 50 parts by mass per 100 parts by mass of the phenolic hydroxyl-containing compound (A).

13. The composition according to claim 12, wherein the composition is a curable composition.

14. A permanent resist film comprising the curable composition according to claim 13.

15. The composition according to claim 11, wherein the curing agent (B2) constitutes 0.5 to 20 parts by mass per 100 parts by mass of the phenolic hydroxyl-containing compound (A).

16. The composition according to claim 15, wherein the composition is a curable composition.

17. A permanent resist film comprising the curable composition according to claim 16.

18. The composition according to claim 11, wherein the composition is a curable composition for permanent resist films.

19. A permanent resist film comprising the curable composition according to claim 18 for permanent resist films.

* * * * *